United States Patent [19]
Iwata et al.

[11] Patent Number: 6,130,054
[45] Date of Patent: Oct. 10, 2000

[54] TEST STRIP FOR CREATINE KINASE ACTIVITY MEASUREMENT

[75] Inventors: Ken Iwata; Kazue Kawahara; Hiroshi Nakajima; Hitoshi Kondo, all of Kyoto, Japan

[73] Assignee: Unitika Ltd., Hyogo, Japan

[21] Appl. No.: 09/210,715

[22] Filed: Dec. 14, 1998

[30] Foreign Application Priority Data

Dec. 19, 1997 [JP] Japan .................................... 9-350517

[51] Int. Cl.[7] .............................. C12Q 1/50; C12Q 1/32; C12Q 1/54; G01N 33/53

[52] U.S. Cl. ............................... 435/17; 435/26; 435/14; 435/4; 435/970; 548/250; 548/262.2

[58] Field of Search .................. 435/17, 26, 14, 435/4, 970; 548/250, 262.2

[56] References Cited

U.S. PATENT DOCUMENTS

| | | | |
|---|---|---|---|
| 4,012,286 | 3/1977 | Sanderson et al. | 435/17 |
| 4,215,197 | 7/1980 | Tarbutton | 435/18 |
| 4,247,633 | 1/1981 | Case et al. | 435/17 |
| 4,360,413 | 11/1982 | Lee | 435/17 |
| 5,206,146 | 4/1993 | Misaki et al. | 435/16 |

FOREIGN PATENT DOCUMENTS

| | | | |
|---|---|---|---|
| 0 239 990 A2 | 10/1987 | European Pat. Off. | C12Q 1/00 |
| 0 285 101 A1 | 10/1988 | European Pat. Off. | C12N 9/20 |
| 0 473 101 A1 | 3/1992 | European Pat. Off. | G01N 33/52 |
| 0 761 821 A1 | 3/1997 | European Pat. Off. | C12Q 1/52 |
| 1323521 | 7/1973 | United Kingdom | G01N 31/14 |
| WO 96/34271 | 10/1996 | WIPO | G01N 21/00 |

*Primary Examiner*—Louise N. Leary
*Attorney, Agent, or Firm*—Sughrue, Mion, Zinn, Macpeak & Seas, PLLC

[57] ABSTRACT

Test strips by which creatine kinase activity can be quantitatively measured at a high sensitivity within a broad measuring range and which have excellent storage stability. Particularly, test strips for the measurement of creatine kinase activity, which comprises a carrier, a dehydrogenase, a diaphorase, NAD or NADP, and a water-soluble tetrazolium compound.

13 Claims, 3 Drawing Sheets

TEST STRIP FOR CREATINE KINASE ACTIVITY MEASUREMENT

FIELD OF THE INVENTION

This invention relates to a test strip for the measurement of creatine kinase activity in samples.

BACKGROUND OF THE INVENTION

In stead of the conventionally used organic chemical reagents, reagents developed making use of enzyme reactions have been broadly applied in recent years to the inspection and diagnosis of morbid states.

These enzyme reaction-aided reagents use the property of enzymes to convert certain components in the living body into detectable substances in specific fashion, that is, they are used generally in a process in which a substance to be measured (A) is converted into an intermediate product (I-1) using an enzyme (a) specific for the substance, further converted into an intermediate product (I-2) by the action of an enzyme (i-1) specific for the intermediate product (I-1) and finally converted into a detectable substance (F) by repeating these steps, and then the detectable substance (F) is quantitatively measured based on the changes in color tone by using a spectrophotometer or by comparing and matching colors with references.

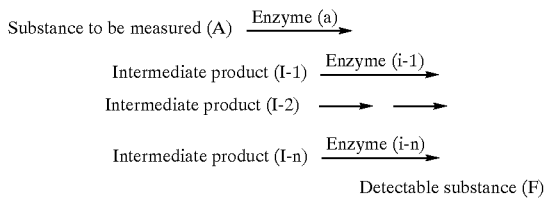

In these reagents, NAD or its reduced form (NADH) and its analogous compound NADP or its reduced form (NADPH) are broadly used as the detectable substance (F) (when these compounds are named generically, they are referred to as "nicotine nucleotides" hereinafter), and these nicotine nucleotides show changes in their absorbance at an ultraviolet region (around 340 nm), so that a reagent in which formed or decreased nicotine nucleotides are measured using a spectroscope has been proposed. Also, a number of reagents have been reported in which a tetrazolium compound is converted into its corresponding formazan by the action of a diaphorase upon formed NADH or NADPH and the resulting formazan is measured at a visible region (e.g., bile acid (JP-A-60-214900; the term "JP-A" as used herein means an "unexamined published Japanese patent application") and *Clinical Chemistry* (a Japanese journal), vol. 19, pp. 290–299 (1990)), triglyceride (JP-A-55-14899), alcohol (JP-B-4-3947; the term "JP-B" as used herein means an "examined Japanese patent publication"), amylase (JP-B-63-37640), creatine kinase (JP-A-58-16699), NAD(P)H (JP-B-4-70000), polyamine (JP-B-6-68490), glucose (JP-B-7-34757) and benzylamine (JP-A-7-184693)). In addition, test strips for the measurement of creatine kinase activity have also been reported (JP-A-63-283600, JP-B-6-95959 and JP-A-1-320999).

However, these reagents use dichlorophenolindophenol (to be referred to as "DCIP" hereinafter), Tetrazolium Blue, Neotetrazolium Blue, MTT, INT or Nitrotetrazolium Blue as the color reagent.

Among these color reagents, DCIP is not suitable for the preparation of test strips, because its colored state by the action of a diaphorase changes into colorless state.

Also, the tetrazolium compounds used as the other color reagents have low solubility in water so that test strips cannot be prepared easily (cf. Comparative Examples below) and, even if it is processed into the form of a test strip, sufficient measuring range cannot be obtained so that additional steps such as dilution of the samples to be measured and the like are required (e.g., *Journal of medical Technology*, vol. 11. No. 6, pp. 496–505, describes that creatine kinase activity can be measured only up to 1,000 units/l even when samples are diluted by a factor of 9).

In addition, since the samples to be tested such as blood, urine and the like are aqueous substances, such test strips have a problem in that measurement of the activity with high sensitivity and good reproducibility is extremely difficult to effect even if reflected light of a sample to be tested is measured by directly adding it to the test strip.

On the other hand, with regard to other cases than creatine kinase and the like enzymes, there is a case in which a reducing type color former is used in test strips for the measurement of magnesium as an inorganic substance, and tetrazolium salts are cited as examples of the reducing type color former (e.g., JP-A-9-266796 and JP-A-9-266797), but only Tetrazolium Violet among the exemplified tetrazolium salts is a tetrazolium salt having high water-solubility and all of the rest have low solubility in water. In addition, since spontaneous coloring occurs when other typical water-soluble tetrazolium compounds are used in such test strips, it has been considered that the use of water-soluble tetrazolium compounds in such test strips as color reagents is not appropriate.

SUMMARY OF THE INVENTION

In view of the above, it therefore becomes an object of the present invention to provide a test strip which can measure creatine kinase activity at a high sensitivity within a broad measuring range through the measurement of reflected light.

With the aim of resolving the aforementioned problems, the inventors of the present invention have conducted extensive studies and, as a result, found that it is possible to prepare a test strip for the measurement of creatine kinase activity in which a water-soluble tetrazolium compound which had been considered to be unsuitable for test strips in the prior art can be used and that such a test strip can measure creatine kinase activity unexpectedly at a high sensitivity within a broad measuring range by the use of the water-soluble tetrazolium compound. The present invention has been accomplished on the basis of these findings. Accordingly, the gist of a first invention resides in a test strip for creatine kinase activity measurement, which comprises a carrier, a dehydrogenase, a diaphorase, NAD or NADP, and a water-soluble tetrazolium compound.

Also, a second invention resides in the just described test strip wherein the water-soluble tetrazolium compound is 2-(4-iodophenyl)-3-(4-nitrophenyl)-5(2,4-disulfophenyl)-2H-tetrazolium, 2-(4-nitro,2-methoxyphenyl)-3-(4-nitrophenyl)-5-(2,4-disulfophenyl)-2H-tetrazolium, 2,3,5-triphenyl-2H-tetrazolium or 2,5-diphenyl-3-(1-naphthyl)-2H-tetrazolium.

Other objects and advantages of the present invention will be made apparent as the description progresses.

DETAILED DESCRIPTION OF THE INVENTION

Figure 1:
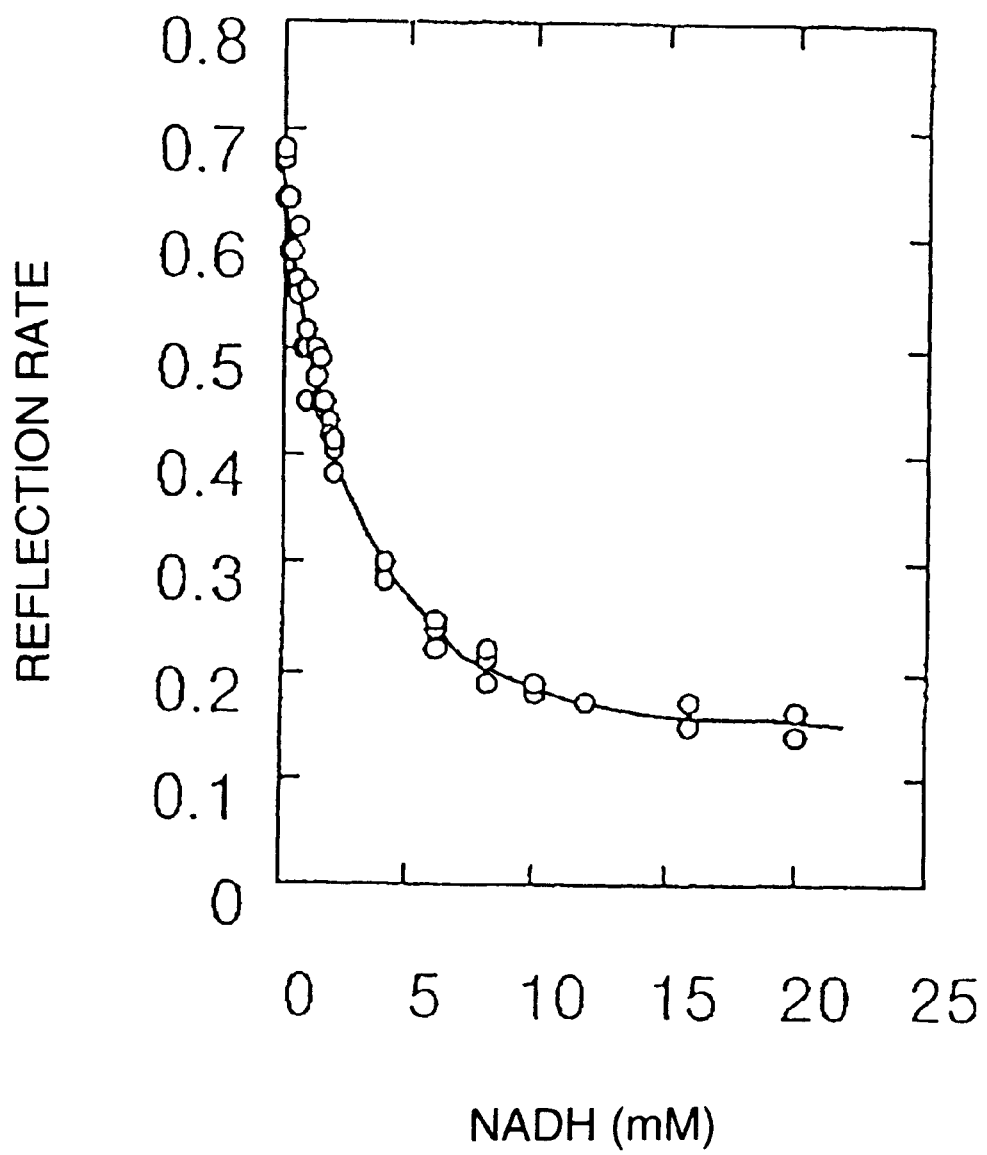
FIG. 1 is a graph showing a relationship between NADH concentration and reflectance when concentration of NADH was measured using a test strip to which WST-8 was added as the tetrazolium compound.

The dehydrogenase to be used in the present invention is not particularly limited, with the proviso that it is a dehydrogenase which acts upon glucose-6-phosphate in a specific fashion, and glucose-6-phosphate dehydrogenase can be cited as its example. Also, biological species and the like materials as its supply sources are not particularly limited, and their examples include those which are originated from lactic acid bacteria, the genus Zymomonas and the like microorganisms.

The water-soluble tetrazolium compound to be used in the present invention is not particularly limited, with the proviso that its solubility in water is 5 mM or more and it develops a color by its reduction by the action of a diaphorase in the presence of NADH or NADPH, and its illustrative examples include 2-(4-iodophenyl)-3-(4-nitrophenyl)-5-(2,4-disulfophenyl)-2H-tetrazolium, 2-(4-nitro,2-methoxyphenyl)-3-(4-nitrophenyl)-5-(2,4-disulfophenyl)-2H-tetrazolium, 2,3,5-triphenyl-2H-tetrazolium and 2,5-diphenyl-3-(1-naphthyl)-2H-tetrazolium, as well as 2-(4-iodophenyl)-3-(2,4-dinitrophenyl)-5-(2,4-disulfophenyl)-2H-tetrazolium, 2-(2-methoxy,4-carboxyphenyl)-3-benzothiazyl-5-(4-sulfoethylaminocarbonylphenyl)-2H-tetrazolium, 3,3'-[3,3'-dimethoxy-(1,1'-biphenyl)-4,4'-diyl]-bis[2-benzothiazyl-4-(4-disulfoethylaminocarbonylphenyl)-tetrazolium] and the like. These water-soluble tetrazolium compounds are available as commercial products or samples from Dojindo Laboratories or Sigma-Aldrich under respective commercial names of WST-1, WST-8, Tetrazolium Red (to be referred to as "TR" hereinafter), Tetrazolium Violet (to be referred to as "TV" hereinafter), WST-3, WST-4 and WST-5. Among these water-soluble tetrazolium compounds, WST-1, WST-8, TR and TV are particularly desirable because of their ability to be immobilized uniformly on the test strip. Furthermore, WST-1, WST-8 and TR are extremely desirable because they are easily solved in aqueous liquids or solutions and can be contained in an sufficient amount on the test strip.

Structural formulae of WST-1, WST-8, TR and TV are shown in the following.

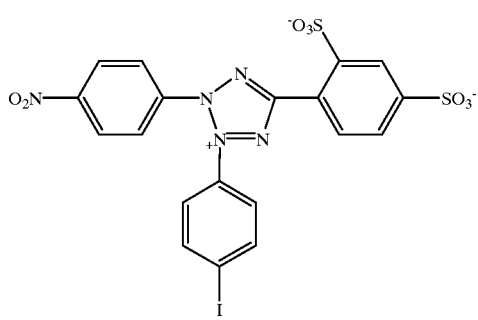

WST-1

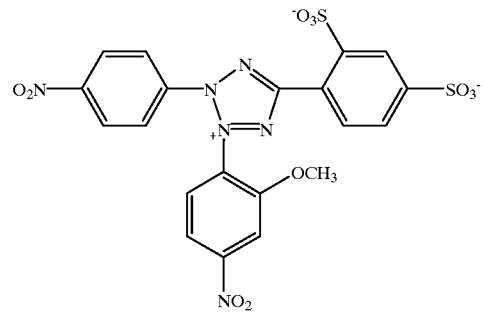

WST-8

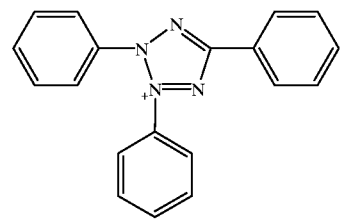

TR

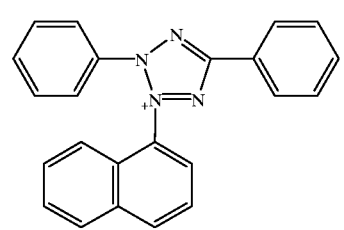

TV

With regard to the diaphorase to be used in the present invention, biological species and the like materials as its supply source are not particularly limited, with the proviso that the enzyme derived therefrom can catalyze the aforementioned reaction, and its examples include those which are produced by *Bacillus stearothermophilus, Clostridium kluyveri* and the like microorganisms or derived from swine heart and the like. In particular, it is desirable to use a diaphorase produced by a thermophilic microorganism, illustratively a diaphorase produced by *Bacillus stearothermophilus,* because of its excellent storage stability.

Also, in order to improve accuracy of the measurement of creatine kinase activity, it is desirable to use a diaphorase which has a reaction equilibrium constant (K value) of 1 or more, preferably 10 or more, more preferably 100 or more, in the direction of from a tetrazolium and a reduced form nicotine nucleotide (NADH or NADPH) to a formazan and an oxidized form of nicotine nucleotide (NAD or NADP) as calculated by the following formula, for example, it is desirable to use the diaphorase I or diaphorase II produced by *Bacillus stearothermophilus.*

$$K = \frac{[\text{oxidized form of nicotine nucleotide}][\text{tetrazolium}]}{[\text{reduced form of nicotine nucleotide}][\text{formazan}]}$$

It is desirable to formulate these components in such amounts that the enzyme reactions starting from the creatine kinase-related reaction to the formation of formazan progress in a quantity of 70% or more, preferably 90% or more, more preferably 95% or more, and an enzyme solution having a diaphorase concentration of from 0.1 to 1,000,000 units/l, preferably from 0.1 to 10,000 units/l, more preferably 1 to 1,000 units/l, may be included in the test strip in an amount of from 0.1 to 10,000 μl, preferably from 1 to 1,000 μl, more preferably from 1 to 100 μl, per 100 cm² test strip. Also, the dehydrogenase may be used in a concentration similar to that of the diaphorase. With regard to NAD or NADP, its solution having a concentration of preferably from 0.001 nM to 200 mM, more preferably from 0.1 nM to 50 mM, may be included in the test strip in an amount of from 0.1 to 10,000 μl, preferably from 1 to 1,000 μl, more preferably from 1 to 100 μl, per 100 cm² test strip.

With regard to the amount of the water-soluble tetrazolium compound, it may be included in an amount of from 0.01 to 500 mg, preferably from 0.1 to 100 mg, more preferably from 0.1 to 50 mg, per 100 cm² test strip. Amounts of the water-soluble tetrazolium compound if too small would cause insufficient color development and if too large would make the compound insoluble thereby entailing reduced accuracy of the measurement.

Illustratively, when the creatine kinase activity is measured, enzymes and substrates may be included in accordance, for example, with the following reaction formula.

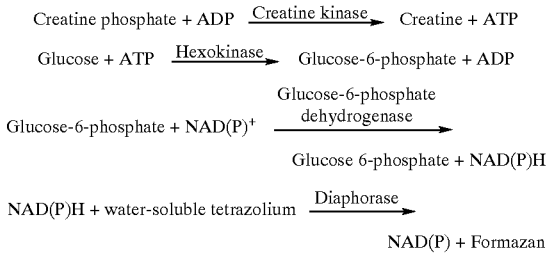

In this case, the test strip contains, at least, dehydrogenase and diaphorase as the enzymes, and NAD or NADP, water-soluble tetrazolium compound as the substrates. Another enzymes, such as hexokinase or glucokinase and the like, and another materials, such as creatine phosphate, ADP, glucose and the like, may be added in the test strip, in case of need. Furthermore, another materials, such as ascorbic acid oxidase, N-acetylcysteine, magnesium ion and the like can be jointly present in the test strip, in case of need.

When the above-described enzymes, substrates, etc. are contained in the test strip of the present invention, all of the enzymes, substrates, etc. which are required to constitute the test strip may be contained in the carrier which constitutes the test strip.

All of the required enzymes, substrates, etc. may be contained into the same part of the carrier, or a part of them is contained into a certain part of the carrier and the remaining materials may be separately contained in a different part of the carrier.

In view of the storage stability, it is preferable in some cases that N-acetylcysteine and water-soluble tetrazolium compound are separately contained in different parts of the carrier. When glucose-6-phosphate dehydrogenase is used as the dehydrogenase, it is preferable in some cases for the same reason that glucose and glucose-6-phosphate dehydrogenase are separately contained in different parts of the carrier. In addition, it is preferable in some cases for the same reason that magnesium ions and dehydrogenase are separately contained in different parts of the carrier, and NAD and creatine phosphate are separately contained in different parts of the carrier.

In this case, concentration of each enzyme to be jointly present in the test strip may be within the same range of the concentration of diaphorase. Also, with regard to the concentration of NAD, NADP, ADP or the like reagent, a solution of each reagent having a concentration of from 0.1 to 100 mM, preferably from 0.1 to 20 mM, may be included in an amount of from 0.1 to 10,000 μl, preferably from 1 to 1,000 μl, more preferably from 1 to 100 μl, per 100 cm² test strip.

According to the present invention, a pH-adjusting buffer, an activation agent, a stabilizing agent, a viscosity-improving agent and the like additive agents may be contained in the test strip.

Examples of the buffer include potassium phosphate, imidazole and the like, as well as certain items of Good's buffer such as 2-morpholinoethanesulfonic acid (MES), N,N-bis-(2-hydroxyethyl)-2-aminoethanesulfonic acid (BES) and the like.

As the activating agent, nonionic, anionic or cationic surface active agents, such as Triton X-100, Tween 20, may be used. These activating agents contribute to the storage stability of test strips and reduction of blank value. With regard to the concentration of these activating agents, a solution having a concentration of from 0.001 to 20%, preferably from 0.01 to 5%, may be included in an amount of from 0.1 to 10,000 μl, preferably from 1 to 1,000 μl, more preferably from 1 to 100 μl, per 100 cm² test strip.

Examples of the stabilizing agent to be used include bovine serum albumin and the like proteins, maltose, glucose, sucrose and the like saccharides, polyethylene glycol and the like high molecular compounds and magnesium, potassium, calcium and the like metal ions. These metal ions also act as enzyme activators. Also useful are ethylenediaminetetraacetic acid (EDTA), ethylene glycol (β-aminoethyl ether)tetraacetic acid (EGTA) and the like. With regard to the concentration of these stabilizing agents, a solution containing a saccharide within the range of from 0.1 to 50% by weight, preferably from 1 to 25% by weight, containing a protein within the range of from 0.001 to 50% by weight, preferably from 0.1 to 25% by weight, containing a metal ion within the range of from 0.001 to 10 mM, preferably from 0.1 to 10 mM, or containing EDTA or EGTA within the range of from 0.001 to 10 mM, preferably from 0.1 to 2 mM, may be included in an amount of from 0.1 to 10,000 μl, preferably from 1 to 1,000 μl, more preferably from 1 to 100 μl, per 100 cm² test strip.

When the above-described additives such as activating agents, stabilizing agents, etc. are contained in the test strip of the present invention, the additives and the necessary enzymes, substrates, etc. may be contained in the carrier which constitutes the test strip.

All of the required enzymes, substrates, additives, etc. may be contained into the same part of the carrier, or a part of them is contained into a certain part of the carrier and the remaining materials may be separately contained in a different part of the carrier.

When EDTA is contained in the test strip of the present invention together with creatine phosphate and N-acetylcysteine, it is preferable in some cases in view of the storage stability that EDTA and creatine phosphate or N-acetylcysteine are separately contained in different parts of the carrier.

With regard to the carrier to be used in the test strip of the present invention, conventional carriers made of high molecular materials can be used, and their illustrative examples include paper and non-woven fabric made of natural fibers or synthetic fibers, membrane films (e.g., membrane filters) and the like. Examples of the membrane films include a nitrocellulose membrane, a cellulose acetate membrane, a polyvinyl alcohol membrane and the like, having a pore size of approximately from 0.1 to 0.5 micron.

The samples to be measured by the test strip of the present invention are not particularly limited. The aqueous liquids, such as the biological materials including blood, serum, plasma, urine and the like, may be used for the measurement of the creatine kinase activity.

The test strip of the present invention can be prepared for example in the following manner. That is, it can be prepared by dissolving the aforementioned components in water, a buffer solution or the like medium, impregnating a carrier with the resulting solution and then thoroughly removing moisture of the carrier by freeze drying or the like means.

The resulting test strip in this manner may be used by cutting it into small pieces or by sticking it to another carrier to be used in a cassette like shape. Also, it is possible to process it on a pad.

Measurement of the creatine kinase activity in biological components using the test strip of the present invention can be carried out for example in the following manner.

That is, (1) a predetermined amount of a sample containing creatine kinase activity to be measured is spotted on the test strip. (2) After a lapse of a predetermined period of time from the dropwise addition of the sample and sufficient impregnation of the test strip with the sample is confirmed, then light of a predetermined wave length is irradiated to measure the reflected light strength using an appropriate reflected light measuring apparatus. (3) Thereafter, a calibration curve is prepared by measuring standard amounts of the creatine kinase activity to be measured in the same manner, and creatine kinase activity in the sample is calculated from the resulting calibration curve.

Examples of the present invention are given below by way of illustration and not by way of limitation.

The Bacillus stearothermophilus diaphorase I (Product No. 100436) and II (Product No. 100437) and glucokinase (Product No. 120387) used in the present invention was purchased from Seikagaku Kogyo. The Clostridium kluyveri diaphorase (Product No. D5540) and the swine heart diaphorase (Product No. D3752) were purchased from Sigma.

Hexokinase (Product No. 1426362), glucose-6-phosphate dehydrogenase (to be referred to as "G6PDH" hereinafter; Product No. 737208) and creatine kinase (Product No. 126969) were purchased from Boehringer-Mannheim.

The enzyme activities described in the attached instructions or on labels of purchased products were used as such.

Tetrazolium Blue (to be referred to as "TB" hereinafter; Product No. 1871-22-3), Neotetrazolium Blue (to be referred to as "NeoTB" hereinafter; Product No. 298-95-3), MTT (Product No. 2348-71-2), INT (Product No. 146-68-9), Nitrotetrazolium Blue (to be referred to as "NTB" hereinafter; Product No. 298-83-9) and WST-1 (Product No. 150849-52-8) were purchased from Dojindo Laboratories. WST-8 was obtained from Dojindo Laboratories as a sample. Nitroblue Tetrazolium (to be referred to as "NBT" hereinafter; Product No. N6876), TV (Product No. T-0174) and TR (Product No. T84859) were purchased from Sigma-Aldrich. Cellulose powder (Product No. 075-41) was purchased from Nakalai Tesque. Other reagents used were all special grade commercial chemicals.

REFERENCE EXAMPLE 1

A solution was prepared by dissolving 50 EM of WST-8 and 10 units/ml of Clostridium kluyveri diaphorase, in final concentrations, in 500 mM imidazole buffer (pH 6.7), and the solution was added in drops to a polyurethane film of 5 mm in width, one drop (about 20 $\mu$l) for each at an interval of about 1 cm, using a peristaltic pump. The film was dried by passing it through a hot air drying zone of about 50° C. (passing time, about 2 minutes) and then test strips were obtained by cutting the film into a size of 5×5 mm using each of the dropped spots as the center. Both termini of each of these test strips was adhered to a form base having a hole of 3×3 mm in size.

A 2 $\mu$l portion of aqueous solution containing a predetermined concentration of NADH was spotted on each of the thus obtained test strips, and reflectance at 550 nm was measured 5 minutes thereafter using a color-difference meter (CR-200, manufactured by Minolta Camera).

The results are shown in FIG. 1 which is a graph showing a relationship between NADH concentration and reflectance. It can be understood from FIG. 1 that NADH can be determined accurately from the reflectance making use of the resulting test strips.

It is also understood from the results that quantitative measurement of optional substances to be measured can be effected by preparing test strips in which various types of dehydrogenase as described in the specification were jointly included.

EXAMPLE 1

A test strip for the determination of creatine kinase was prepared in the following manner.

That is, 30 mM of creatine phosphate, 50 mM of glucose, 5 mM of NAD, 5 mM of ADP, 10 mM of magnesium acetate, 2 mM of EDTA-2Na, 25 mM of NAC and 4% by weight of WST-1, all in final concentration, were dissolved in 100 mM imidazole acetate buffer (pH 6.7). To about 350 $\mu$l portion of this solution were added 2 $\mu$l of about 30,000 units/ml swine diaphorase solution, 10 $\mu$l of 1,650 units/ml G6PDH solution and 1 $\mu$l of 3,600 units/ml hexokinase solution. The resulting solution was added dropwise to a polyethylene terephthalate membrane using Pipette Man and air-dried, and the resulting membrane was coated with 1% by volume methanol solution of a vinyl pyrrolidone-vinyl acetate copolymer (20:80 by weight ratio) and then quickly with a small amount of cellulose powder which was suspended in 50% by volume methanol. By drying this at 40 to 50° C., a test strip supported on a polyethylene terephthalate membrane was obtained.

A 5 $\mu$l portion of a creatine kinase solution was spotted on the thus obtained test strip, and the reflectance was measured at intervals of 30 seconds.

A calibration curve showing a relationship between NADH concentration and reflectance was prepared in the same manner as described in Reference Example 1 except that WST-1 was used instead of WST-8, and changes in the NADH-corresponding amount per unit time were calculated from the measured reflectance using the resulting calibration curve.

Figure 2:
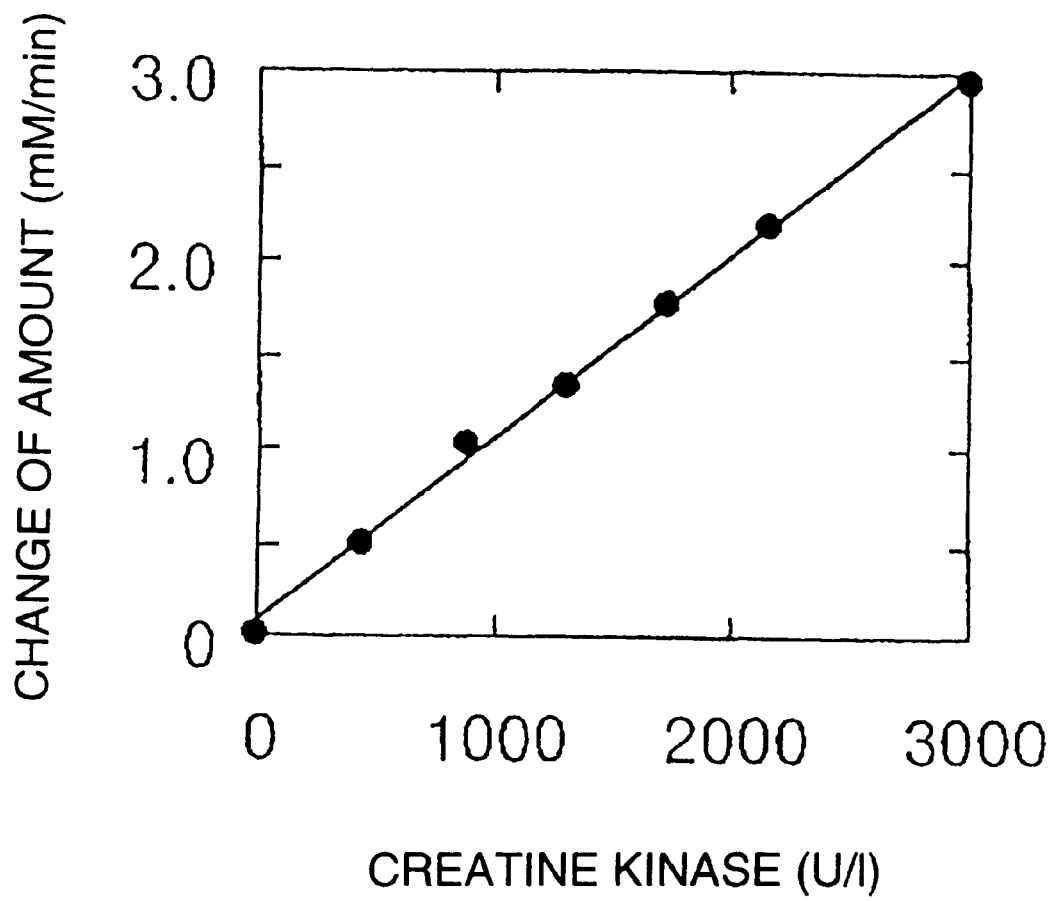
FIG. 2 is a graph showing results of the measurement of creatine kinase activity using the test strip of the present invention.

The results are shown in FIG. 2. FIG. 2 is a graph showing results of the measurement of creatine kinase activity, in which the change in amount corresponding to NADH is plotted as ordinate and the creatine kinase activity as abscissa. It can be understood from this drawing that at least 3,000 units/ml of creatine kinase can be determined by the use of the test strip of the present invention.

EXAMPLE 2

A test strip for the determination of creatine kinase was prepared in the following manner.

That is, 30 mM of creatine phosphate, 50 mM of glucose, 20 mM of NAD, 10 mM of ADP, 10 mM of magnesium acetate, 2 mM of EDTA-2Na, 25 mM of NAC and 5% by weight of TR, all in final concentration, were dissolved in 100 mM imidazole acetate buffer (pH 6.7). To about 350 µl portion of this solution were added 2 µl of about 30,000 units/ml *Bacillus stearothermophilus* diaphorase I solution, 10 µl of 1,650 units/ml G6PDH solution and 2 µl of 2,500 units/ml glucokinase solution. A 2 µl portion of the resulting solution was spotted on a 3×3 mm small piece of Polyflon filter paper (PF050) manufactured by Advantech using Pipette Man and then freeze-dried to obtain a test strip. The thus obtained test strip was adhered to a mount using a pressure sensitive adhesive double coated tape. A 5 µl portion of a creatine kinase solution was spotted on the thus adhered test strip, and the reflectance was measured at intervals of 15 seconds.

A calibration curve showing a relationship between NADH concentration and reflectance was prepared in the same manner as described in Reference Example 1 except that TR was used instead of WST-8, and changes in the NADH-corresponding amount per unit time were calculated from the measured reflectance using the resulting calibration curve.

Separately, the test strip (before spotting of the creatine kinase dilution solution) was covered with aluminum foil and allowed to stand for one month in a dry oven of 37° C. and then a relationship between the concentration of creatine kinase and the changes in the NADH-corresponding amount per unit time was examined in the same manner.

Figure 3:
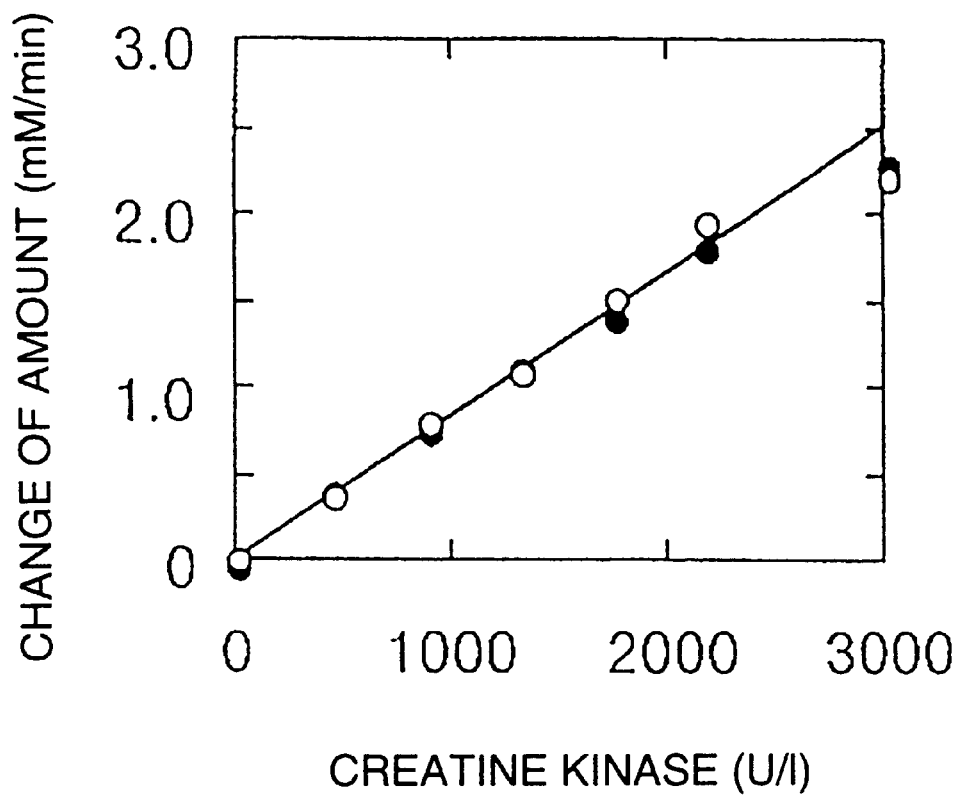
FIG. 3 is a graph showing results of the measurement of creatine kinase activity using the test strip just after its preparation and after one month of storage.

The results are shown in FIG. 3. FIG. 3 is a graph showing results of the measurement of creatine kinase activity using the test strip just after its preparation and after one month of storage, in which ● indicates results when creatine kinase was spotted just after preparation of the test strip and ○ indicates results after one month of storage.

It can be understood from FIG. 3 that at least 3,000 units/ml of creatine kinase can be determined by the use of the test strip of the present invention. It can be understood also that the test strip of the present invention has excellent storage stability.

REFERENCE EXAMPLES 2 TO 5 AND COMPARATIVE EXAMPLES 1 TO 6

Each of the tetrazolium compounds shown in Table 1 in final concentration of 30 mM and 10 units/ml of *Bacillus stearothermophilus* diaphorase II were dissolved in 100 mM imidazole buffer (pH 6.7), and a 3 µl portion of the resulting solution was spotted on a filter paper (No. 2) of 6 mm in diameter manufactured by Whatman and dried to prepare respective test strips.

A paper disc of 8 mm in diameter (manufactured by Advantech, Production No. 49005010) impregnated with 5 mM NADH solution was quickly contacted horizontally with each of the resulting test strips, and the condition of color development on the test strip one minute thereafter was observed with the naked eye.

The results are shown in Table 1.

TABLE 1

| Tetrazolium compounds | Coloring condition |
| --- | --- |
| Reference Example 2: WST-1 | uniform |
| Reference Example 3: WST-8 | uniform |

TABLE 1-continued

| Tetrazolium compounds | Coloring condition |
| --- | --- |
| Reference Example 4: TR | uniform |
| Reference Example 5: TV | uniform |
| Comparative Example 1: TB | irregular |
| Comparative Example 2: NeoTB | irregular |
| Comparative Example 3: INT | irregular |
| Comparative Example 4: NTB | irregular |
| Comparative Example 5: NBT | irregular |
| Comparative Example 6: MTT | irregular |

As is evident from the results shown in Table 1, when the water-soluble tetrazolium compounds WST-1, WST-8, TR and TV were used, the pigments were uniformly immobilized on the test strips.

With regard to the facilitation of test strip preparation, the test strips of Reference Examples were easy to prepare in comparison with the test strips of Comparative Examples.

EXAMPLE 3

A test strip for the determination of creatine kinase was prepared in the following manner.

That is, 25 mM of creatine phosphate, 25 mM of glucose, 2 mM of NADP, 2 mM of ADP, 5 mM of magnesium acetate, 2 mM of EDTA-2K, 30 mM of NAC, 12% by weight of Tween 20 and 1% by weight of WST-1, all in final concentration, were dissolved in 150 mM imidazole acetate buffer (pH 6.6). To about 350 µl portion of this solution were added *Bacillus stearothermophilus* diaphorase I solution, G6PDH and glucokinase to respective final concentrations of about 500 units/ml, 10 units/ml and 10 units/ml. A 2 µl portion of the resulting solution was spotted on a cellulose acetate membrane of 6 mm in diameter manufactured by Advantech (Product No. A045A090C) using Pipette Man and then freeze-dried to obtain a test strip.

A paper disc of 8 mm in diameter (manufactured by Advantech, Production No. 49005010) impregnated with about 3,000 units/l of creatine kinase solution was quickly contacted horizontally with the resulting test strip, and the creatine kinase activity was determined by periodically measuring the reflectance in the following manner.

A calibration curve showing a relationship between NADH concentration and reflectance was prepared in the same manner as described in Reference Example 1 except that WST-1 was used instead of WST-8, and the creatine kinase activity was calculated from the reflectance using the resulting calibration curve, by examining its relationship with changes in the NADH-corresponding amount per unit time. The measurement was repeated four times to confirm its reproducibility.

As the result of the measurement, the activity of creatine kinase was found to be 3,176±0 units/l.

EXAMPLE 4

The activity of creatine kinase was calculated in the same manner as described in Example 3, except that WST-8 was used instead of WST-1, and its reproducibility was confirmed.

As the result of the measurement, the activity of creatine kinase was found to be 2,948±61 units/l.

EXAMPLE 5

The activity of creatine kinase was calculated in the same manner as described in Example 3, except that TR was used instead of WST-1, and its reproducibility was confirmed.

As the result of the measurement, the activity of creatine kinase was found to be 2,906±109 units/l.

EXAMPLE 6

The activity of creatine kinase was calculated in the same manner as described in Example 3, except that TV was used instead of WST-1, and its reproducibility was confirmed.

As the result of the measurement, the activity of creatine kinase was found to be 2,948±61 units/l.

COMPARATIVE EXAMPLE 7

The activity of creatine kinase was calculated in the same manner as described in Example 3, except that TB was used instead of WST-1, and its reproducibility was confirmed.

As the result, it was unable to prepare a test strip due to formation of precipitate in the reagent.

COMPARATIVE EXAMPLE 8

The activity of creatine kinase was calculated in the same manner as described in Example 3, except that NeoTB was used instead of WST-1, and its reproducibility was confirmed.

As the result of the measurement, the activity of creatine kinase was found to be 1,623±524 units/l, showing large dispersion of the measured value. Also, color development on the test strip was irregular when observed with the naked eye.

COMPARATIVE EXAMPLE 9

The activity of creatine kinase was calculated in the same manner as described in Example 3, except that INT was used instead of WST-1, and its reproducibility was confirmed.

As the result of the measurement, the activity of creatine kinase was found to be 1,514±46 units/l showing large dispersion of the measured value. Also, color development on the test strip was extremely thin and irregular when observed with the naked eye.

COMPARATIVE EXAMPLE 10

The activity of creatine kinase was calculated in the same manner as described in Example 3, except that NTB was used instead of WST-1, and its reproducibility was confirmed.

As the result, it was unable to prepare a test strip due to formation of precipitate in the reagent.

COMPARATIVE EXAMPLE 11

The activity of creatine kinase was calculated in the same manner as described in Example 3, except that NBT was used instead of WST-1, and its reproducibility was confirmed.

As the result, it was unable to prepare a test strip due to formation of precipitate in the reagent.

COMPARATIVE EXAMPLE 12

The activity of creatine kinase was calculated in the same manner as described in Example 3, except that MTT was used instead of WST-1, and its reproducibility was confirmed.

As the result, it was unable to carry out the measurement due to extremely large dispersion of the measured value. Also, color development on the test strip was irregular when observed with the naked eye.

The results of Examples 3 to 6 and Comparative Examples 7 to 12 showed that the activity of creatine kinase was able to be measured by the test strips of the present invention in which water-soluble tetrazolium compounds were used, whereas, when other tetrazolium compounds were used, test strips could not be prepared due to formation of precipitate in the reagents or, even if the test strips could be prepared, the activity of creatine kinase could not be measured due to inhibition of the reaction or large irregularity of the color development.

In addition, with regard to the facilitation of test strip preparation, the test strips of the present invention were easy to prepare in comparison with the test strips of Comparative Examples.

Thus, as described above, the test strips of the present invention can measure creatine kinase activity within a broad measuring range. Also, the test strips of the present invention have excellent storage stability.

While the invention has been described in detail and with reference to specific embodiments thereof, it will be apparent to one skilled in the art that various changes and modifications can be made therein without departing from the spirit and scope thereof.

This application is based on Japanese patent application No. Hei-9-350517, filed on Dec. 19, 1997, and incorporated therein by reference.

What is claimed is:

1. A test strip for measurement of creatine kinase activity in a sample, which comprises a carrier, a dehydrogenase, a diaphorase, NAD or NADP, a water-soluble tetrazolium compound and a hexokinase.

2. The test strip according to claim 1, wherein said hexokinase is glucokinase.

3. The test strip according to claim 1, which further comprises creatine phosphate.

4. The test strip according to claim 1, which further comprises ADP.

5. The test strip according to claim 1, which further comprises glucose.

6. The test strip according to claim 1, wherein said water-soluble tetrazolium compound is selected from the group consisting of 2-(4-iodophenyl)-3-(4-nitrophenyl)-5-(2,4-disulfophenyl)-2H-tetrazolium, 2-(4-nitro,2-methoxyphenyl)-3-(4-nitrophenyl)-5-(2,4-disulfophenyl)-2H-tetrazolium, 2,3,5-triphenyl-2H-tetrazolium and 2,5-diphenyl-3-(1-naphthyl)-2H-tetrazolium.

7. The test strip according to claim 1, wherein said carrier is selected from the group consisting of paper, non-woven fabric and a membrane film.

8. The test strip according to claim 1, wherein the amount of said water-soluble tetrazolium compound is from 0.01 to 500 mg per 100 $cm^2$ of the test strip.

9. The test strip according to claim 8, wherein the amount of said water-soluble tetrazolium compound is from 0.1 to 100 mg per 100 $cm^2$ of the test strip.

10. The test strip according to claim 9, wherein the amount of said water-soluble tetrazolium compound is from 0.1 to 50 mg per 100 $cm^2$ of the test strip.

11. The test strip according to claim 1, impregnated with (i) a diaphorase solution having an activity of from 0.1 to 1,000,000 units per liter in an amount of from 1 to 1,000 µl per 100 $cm^2$ of the test strip; and (ii) a dehydrogenase solution having an activity of from 0.1 to 1,000,000 units per liter in an amount of from 1 to 1,000 µl per 100 $cm^2$ of the test strip.

12. The test strip according to claim 1, impregnated with NAD or NADP solution having a concentration of from 0.001 to 200 mM in an amount of from 0.1 to 10,000 µl per 100 cm² of the test strip.

13. A method for measuring creatine kinase activity in a sample, said method comprising the steps of:

(1) spotting a predetermined amount of a sample on the test strip, said test strip comprising a carrier, a dehydrogenase, a diaphorase, NAD or NADP, a water-soluble tetrazolium compound and a hexokinase, (2) after sufficient soaking of the sample in the test strip, the reflected light strength is measured by irradiating the test strip at predetermined intervals with a light source of a specified wavelength, and (3) the creatine kinase activity in the sample is calculated using a calibration curve.

* * * * *